Figure 1:
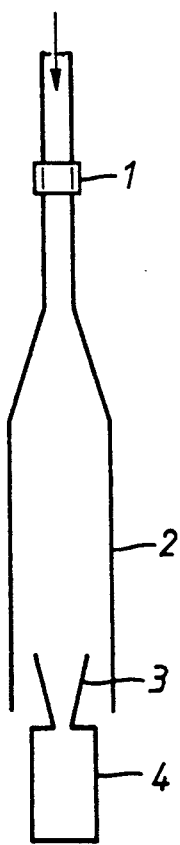

US005254330A

United States Patent [19]
Ganderton et al.

[11] Patent Number: 5,254,330
[45] Date of Patent: Oct. 19, 1993

[54] AEROSOL CARRIERS

[75] Inventors: David Ganderton, Exeter; Nuha M. Kassem, London, both of England

[73] Assignee: British Technology Group Ltd., London, England

[21] Appl. No.: 762,007

[22] Filed: Sep. 20, 1991

[30] Foreign Application Priority Data

Jan. 24, 1990 [GB] United Kingdom ................. 9001635

[51] Int. Cl.[5] ................................................ A61K 9/14

[52] U.S. Cl. ...................................... 424/46; 424/434; 424/435; 424/489; 424/493; 514/169; 514/456

[58] Field of Search ................... 424/45, 46, 489, 493, 424/434, 435; 514/2, 21, 3, 23, 167, 579, 169, 456

[56] References Cited

U.S. PATENT DOCUMENTS

| | | | |
|---|---|---|---|
| 4,199,578 | 4/1980 | Stevenson | 514/180 |
| 4,232,002 | 11/1980 | Nogrady | 424/46 |
| 4,349,542 | 9/1982 | Staniforth | 424/679 |
| 4,409,237 | 10/1983 | Cairns et al. | 514/456 |
| 4,613,500 | 9/1986 | Suzuki | 426/46 |
| 4,847,091 | 7/1989 | Illum | 424/46 |
| 4,940,556 | 7/1990 | MacFarlane | 514/356 |

FOREIGN PATENT DOCUMENTS

WO87/05213 9/1987 PCT Int'l Appl. .

*Primary Examiner*—Thurman K. Page
*Assistant Examiner*—G. S. Kishore
*Attorney, Agent, or Firm*—Nixon & Vanderhye

[57] ABSTRACT

Pharmaceutical excipients useful in dry powder inhalents comprise particles having a rugosity (measured by air permeametry) of less than 1.75. The use of these carriers increases the amount of drug injested by the patient using a dry powder inhaler. The preferred excipients are crystalline sugars such as lactose which may conveniently be prepared by controlled crystallisation from an aqueous medium.

14 Claims, 1 Drawing Sheet

AEROSOL CARRIERS

This invention relates to novel carrier materials useful in the formulation of pharmaceutical compositions especially dry powder compositions which are suitable for use in inhalation aerosols and to novel processes for the production of these materials.

The administration of pharmacological agents by inhalation has been recognised as a valuable technique, particularly in the treatment of diseases of the respiratory tract. The efficacy of the technique has been limited by difficulty in making appropriate dosages available to the lungs. The delivery systems currently available are nebulisers, pressurised metered dose inhalers and dry powder inhalers. Nebulisers are relatively effective but they are expensive and bulky and as a result are mainly used in hospitals. Pressurised metered dose inhalers require good coordination of actuation and inhalation which presents difficulties to many patients. They also require the use of propellants which may be undesirable on environmental grounds. A variety of dry powder inhalers have been developed. All of them rely upon the inspiratory effort of the patient to produce finely divided drug particles which are available to the lungs. Also there have been various proposals for dry powder formulations suitable for use in these inhalers in order to improve the efficacy of the treatment. For example International Patent Application WO 87/05213 describes a carrier which comprises micro-granules of a conglomerate of one or more solid water soluble diluents with a lubricant such as magnesium stearate. In practice another difficulty is caused by the tendency of the drug particles which are necessarily of a relatively small size to agglomerate either with themselves or more usually with particles of the carrier materials with which they are admixed. The difficulties inherent in redispersion of these agglomerates means that only a small proportion of the drug, may be as little as 5% is actually injested via the lungs.

The present invention is directed to novel materials which are useful as carriers in dry powder inhaler compositions. We have discovered that the redispersion of drug particles from compositions comprising carriers is facilitated if the rugosity of the carrier particles is reduced. The rugosity values of the materials are those measured by air permeametry. Accordingly, from one aspect our invention provides a particulate carrier suitable for use in the preparation of pharmaceutical compositions having an average particle size of from 5.0 to 1000 microns and a rugosity of less than 1.75. The measurement of rugosity by air permeametry produces a result which reflects the nature of the external surface of the material under test whereas measurements by techniques such as nitrogen adsorption reflect the total surface area including areas which are not accessible to particulate solids. The rugosity of conventional excipients measured by air permeametry has been found to be at least 1.96 and generally greater than 2.0. The carrier may be any crystalline non toxic material which is acceptable for use in pharmaceutical compositions which does not destabilise the pharmaceutically active materials with which it is formulated and which can be produced in a form having a rugosity of less than 1.75. The preferred carriers are those which are known to be useful in dry powder inhaler compositions especially the mono-saccharides such as lactose, mannitol, arabinose, xylitol and dextrose and their monohydrates, disacharides such as maltose or sucrose and polysaccharides such as starches, dextrins or dextrans.

Preferably the carrier comprises a particulate crystalline sugar such as glucose, fructose, mannitol, sucrose and most preferably lactose.

The average size of the particles of the carrier is preferably in the range 5 to 1000 $\mu$m and more preferably in the range 30 to 250 $\mu$m and most preferably 50 to 100 $\mu$m. Typically at least 95% of the particles will be of a size which falls within this range, although the presence of significant quantities of fine material may be tolerable albeit less preferred.

The particulate sugar crystals which constitute a preferred aspect, may be conveniently prepared by crystallisation from a solution which is preferably an aqueous solution. The conditions under which crystallisation occurs should be controlled so as to favour the production of crystals having the desired low degree of rugosity. In general conditions which allow the crystals to form slowly are preferred whilst those which result in rapid crystallisation are correspondingly less preferred. The utility of any particularly crystallisation process must be evaluated empirically and it is within the skill of the art to modify unsatisfactory procedures in order to produce the desired crystalline form of the novel excipients.

Processes in which a sugar is precipitated from saturated aqueous solution by the addition of at least an equal volume of a water immiscible organic solvent and a quantity of a solvent which is miscible with both water and the aforesaid organic solvent which is at least 5% by volume of the total volume of the aqueous solution and the organic solvent constitute another aspect of this invention. The novel precipitation process may be conveniently carried out by mixing the solution and the solvents at ambient temperature and maintaining them at that temperature with thorough mixing until sugar crystals are formed.

Seeding of the saturated solution may be advantageous insofar as it may reduce the time required for crystal formation.

The size and morphology of the particulate material may be varied by controlling the conditions under which crystallisation and crystal growth occurs. In particular, the choice of the organic water immiscible solvent and the miscible solvent may exert a considerable influence. Examples of water immiscible solvents which may usefully be employed include hexane, chloroform cyclohexane, and toluene. Examples of miscible solvents include acetone, alcohols and acetonitrile The requirement that the miscible solvent is at least partially miscible with the water immiscible solvent (and with water) means that the choice of immiscible and miscible solvents are interdependent. In the case of crystallisation of solutions of lactose, the preferred solvents are hexane (the immiscible solvent) and acetone (the miscible solvent). The quantities of solvent employed are preferably such as to provide an excess volume of immiscible solvent (typically at least 1.25 and more usually at least 1.5 times the volume of the saturated lactose solution being employed) and a relatively small quantity of the miscible solvent, say no more than 20% by volume being employed.

The solvent mixtures are preferably briskly agitated throughout the period of crystallisation and crystal growth. After the crystal growth phase the particles may be recovered by filtration and are usually washed, e.g. with the miscible solvent to remove excess mother liquor prior to drying. The particles may be subject to further washes, e.g. with ethanol and ethanol/water mixtures to improve the purity. These washes also serve to reduce the quantities of very fine particles present in the product which may be preferable.

The form and size of the crystals may be determined by optical and/or scanning electron miscroscopy. The rugosity of the particles may be determined by air permeametry which relates the volumetric flow rate (Q) of air through a packed bed of powder compressed to a known porosity to the internal surface area So of the powder. The rugosity can then be expressed as the ratio So/Sd where Sd is the theoretical surface area (assuming the particles to be spherical). In practice the smoothness of the particles may be readily apparent under the scanning electron microscope and this may render the determination of their rugosity superfluous. Preferably the particles will have a rugosity of no more than 1.5 and most preferably no more than 1.3.

The novel carrier materials are preferably used directly as the sole excipient in dry powder inhalents. However, they may be used in admixture with other excipients although, in general, it is preferred that the excipient comprises at least 80% and preferably at least 95% by weight of the novel carrier materials of this invention.

The novel excipients may be admixed with any suitable pharmacological agent or agents in order to provide a dry powder inhalent composition. Such compositions are believed to be novel and constitute a further aspect of the invention.

The average size of the particles of the pharmacological active agent or agents will be such as to facilitate their passage deep into the lower part of the respiratory tract. In general the average particle size should be within the range 0.1 to 10 microns, more preferably 0.5 to 5.0 microns and at least 95% of the particles should have a size within these preferred ranges.

The amount of pharmacological agent incorporated into the inhalent composition will generally be from 0.1 to 50% by weight of the composition. The amount will vary with the desired dosage of any particular agent. However, the novel compositions have the advantage that a higher proportion of the pharmacological agent is available to the lower part of the respiratory tract and hence the proportion of any particular agent may be reduced, to one half or even one quarter by weight of the composition compared to a conventional formulation. This increased availability of the active agent also enables agents to be administered by oral inhalation which would not previously have been administered by this route. Thus, agents other than those conventionally employed to treat ailments of the respiratory tract may be administered by this means.

Examples of pharmacological agents which have been administered by oral inhalation include agents with an anti-histamine and anti-allergic action such as sodium cromoglycate and ketotifen, $\beta$-agonists, anticholinergies such as ipratropium bromide, oxytropium bromide and thiazinamide chloride, sympathomimetic amines such as terbutaline, salbutamol, clenbuterol, pirbuterol, reproterol, procaterol and fenoterol, steroids especially torticosteroids such as beclamethasone dipropionate, flurisolide budesonide and mucolyties such as ambroxol.

Examples of other pharmacological agents which might usefully be incorporated into the novel compositions of this invention include hypnotics, sedatives, tranquillisers, anti-inflammatory agents, anti-histamines, anti-tussives, anti-convulsants, muscle-relaxants, anti-spasmodics, cardiovascular agents, anti-bacterials such as pentamidine, anti-biotics and hypoglycaemic agents.

Where appropriate the compositions of this invention may contain a bronchodilator as an additional active agent. The amount of any such bronchodilator will normally not exceed the dosage conventionally employed in its application by inhalation and will preferably be less than is conventionally employed. Examples of useful bronchodilators include isoprenaline, rimiterol, ephedrine, ibuterol, isoetharine, fenoterol, carbuterol, clinbuterol, hexaprenaline, salmifamol, soterenol, trimetoquinol, orciprenaline, terbutaline and salbutamol or a pharmaceutically acceptable salt thereof.

The invention finds particular application in the administration of agents which cannot be conveniently administered by other routes. A particular example are peptides such as insulin and growth hormones, ACTH and LHRH analogues.

In addition to the novel carrier and the pharmacologically active agent or agents the compositions of this invention may contain other ingredients such as colouring matter of flavouring agents such as those which are conventionally incorporated into dry powder inhalant compositions. Preferably such ingredients are present in only minor quantities, e.g. less than 10% and more preferably less than 5% by weight of the composition. Such materials will also preferably comprise particles of size comparable with that of the carrier, e.g. 30 to 150 microns.

The compositions may be formulated by dry mixing the active agent and the excipient. The composition may conveniently be encapsulated, e.g. in a hard gelatin capsule suitable for use in the inhalers which are readily available. The compositions may be formulated into capsules containing a single dose of active material which can be inserted into an appropriate inhaler. Alternatively, they may be placed in a larger container and placed in an inhaler which is designed so as to meter a single dose of the composition into its air passage upon activation. The compositions may be dispensed using any of the conventional inhalers. Their use in dry powder inhalers of all types is strongly preferred. Such inhalers which contain a composition according to this invention are novel and form a further aspect of the invention.

A BRIEF DESCRIPTION OF THE DRAWING

FIG. 1 shows the diagram of an apparatus suitable for the use of the inhalent composition.

The invention is illustrated by the following examples.

EXAMPLE 1

Salbutamol sulphate BP was micronised using an air jet mill (Fryma jet mill JM 80) at a pressure of 7.5 bar and a feed rate of 5 g/min. The particle size distribution was determined microscopically by measuring the diameter of 500 particles.

Lactose (lactochem Pharmaceuticals), in a size range of 63-90 $\mu$m was obtained by sieving (Alpine air jet sieve).

Recrystallised lactose was obtained by crystallisation of the original lactose in a partially miscible mixture of water, hexane and acetone.

Lactose was dissolved in water (2 to 1) in a beaker at 80 C. The solution was cooled to room temperature, 75 ml of hexane (Reagent grade) was added to 50 ml of the saturated solution and agitated at 500 rpm with a paddle type agitator with four blades, acetone (10 ml) (Reagent grade) was then added. The mixture was stirred for 8-12 h, during which time lactose crystals formed. These were washed with acetone, absolute ethanol, 60% ethanol in water and absolute ethanol respectively and dried.

The particle size of the recrystallised lactose was determined with the optical microscope and was found to be in the range of 60-90 μm. The examination of the carrier surface was by scanning electron microscopy. The rugosity of the lactose before and after crystallisation was determined by compressing a mass of powder equal to its density to a known porosity in the cell of a Fisher Sub-Sieve Sizer. The flow rate through the bed at a fixed pressure differential is transcribed by the instrument to an average particle diameter dm. The specific surface So was calculated from the equation $$So = \frac{6 \times 10^4}{dm \, p}$$

where p is the powder density. The rugosity before crystallisation was found to be 2.36 whilst the rugosity after recrystallisation was found to be 1.16.

Samples of drug-lactose blends were prepared in a ratio of 1:67.5 by mixing the micronised drug and the treated lactose with a spatula. The homogeneity of the mixtures was verified by the assay of ten 30 mg samples. The coefficient of variation of the sample content ranged between 1.1–3.0 for the mixtures studied. 27.4 mg+1.4 mg of the mixtures containing 400 μg of salbutamol sulphate was filled into hard gelatin capsules (size 3).

SIMULATION OF PATIENT USE

A diagram of the apparatus is shown in FIG. 1. A powder inhaler device (1) (Rotahaler, Allen & Hanbury's Ltd.) containing an encapsulated dose was assembled in a line conducting dried filtered air at up to 200 l/min. On actuation, the powder was blown into a vertical diffuser (2) 550 mm in length with 2 mm and 70 mm inlet and outlet diameters respectively. Sharp edged conical probes (3) with diameters calculated to give isokinetic sampling were placed at midstream of the diffuser. Air was drawn at 28.3 l/min through a sampler (4) (Anderson 1 CFM Ambient) which comprises a preseparator stage that collects particles with an aerodynamic diameter larger than 10 μm, and seven separation stages. Stages 0 to 2 have approximate cut-off diameters of 5.5–10 μm and stages 3 to 7 collect particles less than 5.5 μm. A final filter trapped particles less than 0.4 pm.

Experiments were conducted at air flow rates of 60 and 150 l/min, each using 10 capsules. After deposition, the inhalation device with the capsules, the preseparator, stages 0 to 2, stages 3 to 7 and the filter of the impactor were separately rinsed with methanol and the washings assayed by HPLC using reversed phase column packed with octadecylsilane (30 cm 3.9 mm i.d.) using 35% 0.013 M ammonium acetate in methanol as the mobile phase and a variable wavelength detector set at 276 nm. The total amount of salbutamol sulphate recovered from each stage was calculated and expressed as a percentage of the total dose discharged.

The mass median diameter of salbutamol sulphate was 2.8 μm with a geometric standard deviation of 1.3.

The results of the effect of surface properties of a carrier on drug deposition are shown in Table I.

TABLE I

Percentage of drug deposited at various stages using regular lactose and recrystallised lactose.

| | Regular lactose | Recrystallised lactose |
|---|---|---|
| | At air flow rate of 60 l/min. | |
| Device | 19.7 | 23.8 |
| Preseparator | 57.9 | 33.6 |
| Stages 0-2 | 2.8 | 0.6 |
| Stages 3-7 | 19.6 | 42.0 |
| | At air flow rate of 150 l/min | |
| Device | 15.2 | 24.4 |
| Preseparator | 76.8 | 51.5 |
| Stages 0-2 | 2.6 | 2.6 |
| Stages 3-7 | 5.4 | 22.0 |

EXAMPLE 2

A double blind randomised cross-over trial was carried out to compare the effects of a commercial formulation comprising salbutamol sulphate and a conventional lactose carrier with a composition according to this invention containing the same proportions of salbutamol sulphate and a modified lactose of this invention prepared in the manner described in Example 1. Eleven moderate to severe stable atopic asthmatic patients took part in the trial (FEV,<80% predicted;>15% reversibility. FEV is Forced Expiratory Volume in 1 second). The trial was carried out using conventional dry powder inhalers. The commercial formulation produced a mean increase in FEV, of 21.4%. The formulation according to this invention produced a mean increase in FEV, of 27.5%. The difference 6.1% was significant (paired t-test; p<0.05; confidence interval 0.64–11.52).

What we claim is:

1. A dry powder inhalent composition comprising an effective amount of at least one non-proteinaccous pharmacological agent in admixture with a particulate carrier suitable for use in dry powder inhalent compositions, said carrier comprising particles having an average particle size of from 5.0 to 1000 microns and a rugocity as measured by air permeametry of less than 1.75.

2. A composition according to claim 1, wherein the carrier is a crystalline sugar.

3. A composition according to claim 1, wherein the carrier particles have an average particle size of from 30 to 250 microns.

4. A composition according to claim 1, wherein the carrier particles have a rugocity of not more than 1.5.

5. A composition according to claim 1, wherein the said carrier consists essentially of particles having an average particle size of from 5.0 to a 1000 microns and a rugocity as measured by air permeametry of less than 1.75.

6. A composition according to claim 1 comprising from 0.1 to 50% by weight of said at least one pharmacological agent.

7. A composition according to claim 1, wherein said pharmacological agent is a particulate solid having an average particle size of from 0.1 to 10.0 microns.

8. A composition according to claim 1, wherein said pharmacological agent is selected from the group consisting of a β agonist, a steroid and sodium chromoglycate.

9. A composition according to claim 1, wherein said pharmacological agent is an anti-bacterial agent.

10. A composition according to claim 1 in encapsulated form.

11. A dry powder inhaler device comprising a dry powder inhalent composition according to claim 1.

12. A composition according to claim 2, wherein the crystalline sugar is selected from a group consisting of glucose, fructose, mannitol, sucrose and lactose.

13. A composition according to claim 12, wherein the crystalline sugar is lactose.

14. A composition according to claim 9, wherein said anti-bacterial agent is pentamide.

* * * * *